United States Patent [19]

Boberski et al.

[11] 4,174,229
[45] Nov. 13, 1979

[54] MAGNESIUM OXIDE CEMENTITIOUS COMPOSITIONS CONTAINING HYDROLYZABLE ORGANO-SILICON COMPOUNDS

[75] Inventors: William G. Boberski; Wen-Hsuan Chang, both of Gibsonia; Victor G. Petracca, Apollo; Jerome A. Seiner, Pittsburgh, all of Pa.

[73] Assignee: PPG Industries, Inc., Pittsburgh, Pa.

[21] Appl. No.: 891,110

[22] Filed: Mar. 28, 1978

[51] Int. Cl.$^2$ ............................ C04B 9/02; C04B 9/04
[52] U.S. Cl. .................................. 106/107; 106/18.12; 106/18.21; 106/105; 106/108; 106/194; 106/203; 106/187.11; 106/287.13; 106/287.16; 260/29.65; 260/42.13
[58] Field of Search ............ 106/106, 107, 108, 287.11, 106/287.13, 287.15, 287.16, 194, 203, 105; 260/29.6 S, 42.13

[56] References Cited

U.S. PATENT DOCUMENTS

| | | | |
|---|---|---|---|
| 3,046,242 | 7/1962 | Santelli | 106/287.12 |
| 3,353,975 | 11/1967 | Shannon et al. | 106/107 |
| 3,499,955 | 3/1970 | Shannon | 106/106 |
| 3,753,750 | 8/1973 | Davis | 106/107 |

*Primary Examiner*—Lorenzo B. Hayes
*Attorney, Agent, or Firm*—Charles R. Wilson

[57] ABSTRACT

Cementitious magnesia compositions are disclosed containing at least one of a family of organo-silicon compounds, each of which is characterized in having attached to the silicon atom at least one group hydrolyzable at the silicon atom and at least one group comprising a moiety that is attached to the silicon atom through a substantially non-hydrolyzable silicon-carbon bond. Magnesia compositions containing one of the described organo-silicon compounds, wherein the non-hydrolyzable moiety has a working parameter of solubility, $\delta_{wp}$, typically in the range of about 6.2 to about 8.0 (cal./cc)$^{\frac{1}{2}}$, have improved casting, molding or spraying properties as compared to magnesia compositions lacking the organo-silicon compound.

52 Claims, 6 Drawing Figures

MAGNESIUM OXIDE CEMENTITIOUS COMPOSITIONS CONTAINING HYDROLYZABLE ORGANO-SILICON COMPOUNDS

BACKGROUND OF THE INVENTION

1. Field of the Invention

Cementitious compositions containing mixtures of magnesium oxide (magnesia) and magnesium salts have been known for some time. Of particular interest are magnesia compositions which find utility in spraying, molding and casting applications.

2. Description of the Prior Art

Magnesium oxide based cements are frequently used as fire retardants, usually spray applied to steel and wood structural beams, as filler materials for sandwich-type, insulating wall panels, as flooring or flooring substrate, and for various cast and molded articles where the properties of high heat resistance coupled with light weight and low cost are desired.

The use of magnesia cements as fire-proofing in place of conventional spray-applied asbestos-containing insulation compositions is of special significance in view of recent prohibition in many locales against use of such compositions because of the carcinogenic nature of asbestos. The requirements of costly, heavy-duty hydraulic pumps and sprayers for applying conventional magnesia compositions to walls and beams has, however, retarded use of magnesia cements as fire proofing. Reduction of viscosity by dilution of the compositions with water provides easily sprayable materials, but creates problems of corrosion of substrates, increased curing times and decreased strength properties of cured articles.

Also of increasing interest is the use of magnesia cements as substitutes for natural and synthetic plastics in molding applications, which plastics are derived directly or indirectly from scarce petroleum feedstocks. Cast or molded articles of magnesia in many uses exhibit properties of heat resistance and strength comparable to many organic plastic molded articles. Conventional magnesia cements, however, especially those having fillers or additives, typically have high viscosities and the resulting lack of "pourability" has precluded uses of the compositions for the casting of articles of intricate or complex shape where good flowability of the composition within a mold is a necessity. Adding water to magnesia compositions to reduce the viscosity of a composition to make it pourable or more easily moldable is unsuitable because the increase in volume of the composition produces intolerable degrees of shrinkage or creates voids in the cured product. Additionally, the highest strength magnesia cements are derived from compositions having magnesium salts in saturated or nearly saturated concentrations in water in the wet, pre-cured state; hence, the addition of water may dilute the matrix-forming components to the extent that a solid, integral product cannot form.

Increased use of magnesia compositions would no doubt result if the highly viscous nature of the compositions could be modified to provide more easily sprayable and moldable compositions. Such increased use would generate significant economic benefits inasmuch as magnesia and magnesium-containing salts constitute a significant and practically inexhaustible portion of the material of the earth's natural resources.

SUMMARY OF THE INVENTION

It has now been found that improved materials for molding, casting or spraying purposes may be provided by a cementitious composition comprising (a) magnesium oxide, (b) a magnesium salt having at least moderate solubility in water, (c) at least one organo-silicon compound, and (d) a liquid phase comprising water in an amount effective to cause reaction of at least a portion of the magnesium oxide and at least a portion of the magnesium salt to form a matrix curable to a hardened state, wherein the cementitious composition exhibits a lower viscosity in its stage of initial application as in a mold or as sprayed onto a substrate, than if the organo-silicon compound were absent. The organo-silicon compound is further characterized in having attached to its silicon atom at least one group having a hydrolyzable bond with the silicon atom and at least one group comprising a moiety that is attached to the silicon atom through a substantially non-hydrolyzable silicon-carbon bond. In further description of the invention, the term "non-hydrolyzable moiety" is generally intended to mean that portion of the group attached to the silicon atom by a silicon-carbon bond that is not substantially hydrolyzable at the silicon-carbon bond. Typical organo-silicon compounds useful in the invention are characterizable in having a non-hydrolyzable moiety attached to the silicon atom comprising functional groups which impart to the moiety a solubility property measurable by a working parameter of solubility. This parameter is relatable to decreases in the viscosity of wet magnesia compositions containing the specified organo-silicon compound during application stages as compared with magnesia compositions lacking the organo-silicon compound.

DESCRIPTION OF THE PREFERRED EMBODIMENTS

Typically, magnesia cements comprise a matrix or binder which forms a three-dimensional system of alternating molecular units when the composition is in its solidified or cured form. The binder is derived from bringing together water, at least one magnesium salt having at least moderate solubility in water, and magnesium oxide. Magnesium salts having moderate solubility in water are intended in this context to be those compounds having solubilities greater than one part solute in 1000 parts water solvent. Magnesium oxide, by comparison, has a solubility of $6.2 \times 10^{-5}$ parts per 1000 parts water.

Magnesium salts having at least moderate solubility in water and having been demonstrated as providing suitable magnesia compositions include magnesium chloride hexahydrate, magnesium nitrate hexahydrate, magnesium acetate tetrahydrate and magnesium bromide hexahydrate.

Other magnesium salts having at least moderate solubility in water and which are believed suitable for use in the magnesia compositions of the invention include magnesium acetate, magnesium orthoarsenite, magnesium benzoate, magnesium bromide, magnesium selenate, magnesium silicofluoride, magnesium stannide, magnesium sulphate, magnesium sulphate heptahydrate, magnesium sulphite, magnesium thiosulphate, magnesium thiotellurite, magnesium hypophosphite, magnesium salicylate, magnesium fluosilicate, magnesium fluosilicate hexahydrate, magnesium formate, magnesium iodate, magnesium iodide, magnesium iodide octahydrate, magnesium lactate, magnesium molybdate, magnesium nitrate dihydrate, magnesium nitrite trihydrate, magnesium chlorate, magnesium perchlorate hexahydrate, magnesium chloride, magnesium hydrogen citrate pentahydrate, magnesium cyanide and magnesium ferrocyanide.

It is intended that in place of any of the aforementioned magnesium salts there may be present in the cementitious composition the precursors of these salts; for example, the cementitious composition may contain magnesium hydroxide and hydrochloric acid, the reaction product of which provides a magnesium chloride salt. Thus, where the invention is defined as requiring a magnesium salt, this requirement may be satisfied by the presence in the cementitious composition of suitable precursors reactable to form the magnesium salt.

There may be, of course, more than one of the aforementioned water-soluble magnesium salts present in the composition in combination with the magnesium oxide. The total amount of all magnesium-containing salts in the composition is preferred to be at least that amount which forms a saturated or nearly saturated solution in the water solvent, which compositions thus may be characterized as "high solids" compositions. Generally, the mole ratio of magnesium oxide to soluble magnesium salt is in the range of 3:1 to 10:1. Preferably, the mole ratio range is 6:1 to 7.5:1.

Water of any reasonable purity may be used in which to bring together the magnesium-containing components. The water should be free, however, of any contaminants which inhibit the curing of the cementitious composition or which tend to weaken the cured composition by reacting with constituents of the binder matrix; for example, strong acid species present in the water could react with basic components of the composition and generate heat which would accelerate cure, or could appreciably weaken the cured composition by attacking the basic salts of the matrix. Generally, commonly available tap water is suitable for use in formulation of the composition.

Generally, the amount of water utilized in the compositions is in a mole ratio range of water to magnesium salt of 8:1 to 30:1. Preferably, the mole ratio of water to magnesium salt ranges from 11:1 to 15:1.

The organo-silicon compound may have one, two or three hydrolyzable groups attached to the silicon atom which may be selected from the group consisting of halogen, hydroxyl, alkoxyl, substituted alkoxyl, aryloxyl, substituted aryloxyl, aralkoxyl, substituted aralkoxyl, alkylamino, substituted alkylamino, silylamino, substituted silylamino, mercapto and substituted mercapto radicals. The requirements of one, two or three hydrolyzable groups attached to the silicon atom may be satisifed by the hydrolyzable group being hydroxyl group even though the organo-silicon compound may be substantially the same before and after hydrolysis.

Suitable halogen radicals include chloro, bromo and iodo. Examples of suitable alkoxyl groups include methoxy, ethoxy, propoxy, acetoxy and the like. Suitable substituted alkoxyl groups include chloro, bromo and iodo substituted alkoxyl radicals, where the alkoxyl moiety is of the aforementioned groups. Examples of suitable aryloxy, aralkoxy, substituted aryloxy and substituted aralkoxy groups are, respectively, phenoxy, phenylethoxy, chlorophenylethoxy and phenylchloroethoxy radicals. Suitable alkylamino and substituted alkylamino groups are, respectively, methylamino or dimethylamino and chloromethylamino. Examples of mercapto and substituted mercapto groups include, respectively, ethyl mercapto and chloroethyl mercapto radicals, Silylamino and substituted silylamino groups include those secondary and tertiary amine radicals having a silicon atom bonded to the amino nitrogen.

Decreases in viscosity exhibited by compositions of the invention may be related to a solubility property of a portion of the organo-silicon compound. Generally, the solubility of an organic species may be expressed by its solubility parameter, δ, defined as

$$\delta = \frac{F}{V} \qquad (I)$$

where F is a molar attraction constant of an organic species in (calories-cubic centimers)$^{\frac{1}{2}}$ per mole and V is a molar volume constant of the species in cubic centimeters per mole. Where the organic species comprises one or more chemical groups, a parameter of solubility for the whole organic species may be calculated from the weighted average of the individual chemical groups. Where the constants listed in Table I are used for calculating this parameter of solubility, the result is designated a "working parameter of solubility", $\delta_{wp}$, which may be expressed as

$$\delta_{wp} = \frac{\Sigma F_i}{\Sigma V_i} . \qquad (II)$$

Surprisingly, there has been found a striking correlation between improvements in the casting, molding or spraying properties of magnesia compositions containing an organo-silicon compound that has at least one moiety attached to the silicon atom and which is not hydrolyzable at the moiety-attaching silicon-carbon bond, where this moiety has a working parameter of solubility within a range of about 6.2 to about 8.0 (cal./cc.)$^{\frac{1}{2}}$.

Generally, the group not hydrolyzable at the silicon atom of the organo-silicon compound may comprise a moiety having one or more functional groups selected from a large number of organic radicals, provided that the working parameter of solubility of the moiety is within the specified range. Families of radicals from whch useful moieties may be derived to provide a suitable value of the working parameter of solubility include alkyl or oxalkyl groups which may have such substituted groups as alkyl, alkoxy, aryl, aryloxy, substituted aryloxy, acrylyl, substituted acrylyl, carbohydroxy, carboalkoxy, amino, amido, ureido, epoxy and sulphur. Specific examples are methylene, 1,2-ethylene, 1,2-propylene, 1,3-propylene, 1,2-butylene, 1,3-butylene, 1,4-butylene, 1,2-pentylene, 1,3-pentylene, 1,4-pentylene, 2-ethyl-1,3-propylene, methoxymethylene, 2-ethoxy-methylene, 2-methoxy-1,3-propylene and 2-ethoxy-1,4-butylene; organic acid radicals such as nitrogen-containing radicals such as epoxy radicals such as and divalent thio radical —S—.

The working parameter solubility values for the aforementioned and many other organic functional groups may be calculated from molar attraction and molar volume constants found in the literature. The values set forth in Table I, for example, are drawn from the considerable, empirical and theoretical efforts of Bunn, Hoy and Van Krevelen verifying and expanding upon the earlier work of P. A. Small.

TABLE I

| Chemical Group | Molar Attraction Constant[a] $F_i$(cal.-cc.)$^{\frac{1}{2}}$ | Molar Volume Constant[b] $V_i$(cc.) |
|---|---|---|
| —CH$_2$— | 131.5 | 21.8 |
| —CH$_3$ | 148.3 | 27.8 |
| CH | 86.0 | 13.6[d] |
| —NH$_2$ | 226.6 | 21.1[d] |
| —NH— | 180.0 | 14.6 |
| $\underset{|}{-N-}$ | 61.1 | 8.7[d] |
| —OH | 225.8 | 14.9 |
| —O— (ether) | 115.0 | 7.3 |
| ⌬ | 735.0[c] | 89.9 |
| —CH=CH | 222.0[c] | 16.9[d] |
| CH$_2$=CH— | 301.0[c] | 40.8[d] |
| —SH | 315.0[c] | 29.6[d] |
| —S— | 209.4 | 21.6[d] |
| $\underset{|}{-C=O}$ | 263.0 | 21.6 |
| —COO— | 326.6 | 28.9 |
| —O— (epoxide) | 176.2 | 7.3 |
| $\underset{-HNCO-}{\overset{O}{\underset{\|}{}}}$ | 506.6[e] | 43.5[e] |
| $\underset{H_2NCO-}{\overset{O}{\underset{\|}{}}}$ | 553.2[e] | 50.0[e] |
| $\underset{H_2NCNH-}{\overset{O}{\underset{\|}{}}}$ | 669.6[e] | 57.3[e] |
| $\underset{-HNCNH-}{\overset{O}{\underset{\|}{}}}$ | 623.0[e] | 50.8[e] |
| $\underset{-CNH_2}{\overset{O}{\underset{\|}{}}}$ | 489.6[e] | 42.7[e] |
| $\underset{-CNH-}{\overset{O}{\underset{\|}{}}}$ | 443.0[e] | 36.2[e] |

[a]Values taken from Hoy, J.P.T., 42, 76 (1970), except where indicated.
[b]Values taken from Bunn, J. Poly. Sci., 16, 323 (1955), except where indicated.
[c]Values taken from Small, J. Appl. Chem., 3, 71 (1953).
[d]Values calculated by doubling corresponding molar volume values based on Van Der Waal energy calculations reported by Van Krevelen et al, Properties of Polymers, Elsevier Publishing Co., New York (1972), App. I.
[e]Values developed by adding constants listed in Table I for component portions of each composite chemical group.

Specific organo-silicon compounds having at least one silicon-attached hydrolyzable group and at least one silicon-attached non-hydrolyzable moiety where the moiety has a working parameter of solubility within the range of about 6.2 to about 8.0 (cal./cc.)$^{\frac{1}{2}}$ and which organo-silicon compounds are known to provide magnesia compositions with improved molding, casting or spraying properties, include six commercially available compounds depicted in formulae III through VIII, namely, γ-aminopropyltriethoxysilane (A-1100, Union Carbide):

N-β-aminoethyl-γ-aminopropyltrimethoxysilane (A-1120, Union Carbide):

γ-methacryloxypropyltrimethoxysilane (A-174, Union Carbide):

γ-glycidoxypropyltrimethoxysilane (A-187, Union Carbide):

γ-aminopropylmethyldiethoxysilane (Petrarch Systems):

δ-aminobutyldimethylmethoxysilane (Silar Labs):

(VIII)

Other suitable organo-silicon compounds may be derived from the reaction of a silane having a non-hydrolyzable moiety containing an epoxy group and a compound containing one or more chemical groups having an active hydrogen atom, such as amino, amide, ureido, urea, urethane, thiol, and hydroxyl groups, each having at least one active hydrogen. Or, the organo-silicon compound may be derived from the reaction of an epoxy-containing compound and a silane having a moiety containing groups having an active hydrogen atom, such as an aminosilane, amide-containing silane, ureido-containing silane, urea-containing silane, urethane-containing silane and thiol-containing silane. The epoxy-containing compound may be an aliphatic epoxide such as 1,2-butylene oxide or it may be an aliphatic polyepoxide such as 1,4-butanediol diglycidyl ether.

Other suitable organo-silicon compounds may be derived from the reaction of a compound containing acrylyl or substituted acrylyl groups and a silane having a non-hydrolyzable moiety comprising an amino group containing at least one active hydrogen. Or, suitable organo-silicon compounds may comprise the reaction products of an amino-compound having at least one active hydrogen and a silane having a non-hydrolyzable moiety comprising acrylyl or substituted acrylyl groups.

Preferred organo-silicon compound reaction products may be derived from the reaction of aminoalkylsilanes, such as those illustrated in formulae III, IV, VII and VIII, with 1,2-butylene oxide. For example, the reaction of γ-aminopropyltriethoxysilane and 1,2-butylene oxide in varying molar ratios may provide a mixture comprising in varying amounts organo-silicon reaction products believed to have the structures depicted in formulae IX, X and XI, which mixture is suitable for use in cementitious compositions of the invention:

(IX)

(X)

(XI)

Another useful organo-silicon compound may be derived from reacting in approximately 2 to 1 molar ratio γ-aminopropyltriethoxysilane and 1,4-butanediol diglycidyl ether which provides a reaction product comprising a compound having two silicon atoms per molecule believed to have the structure depicted in formula XII:

(XII)

It should be noted that for any organo-silicon compound useful in the invention where two silicon atoms are present in the molecule, as illustrated in formula XII, the moiety chosen to derive a working parameter of solubility excludes silicon. Hence, for the formula XII compound the non-hydrolyzable moiety is that portion of the group comprising the segment in the chain between the two silicon atoms.

It has also been found that organo-silane compounds having both a hydrolyzable group and non-hydrolyzable moiety attached to a silicon atom and which are observed to be substantially ineffective in improving the spraying, casting or molding properties of magnesia compositions can be made effective by reacting the organo-silane compounds with epoxide-containing compounds. For example, while both ureidopropyltriethoxysilane (A-1160, Union Carbide) and mercaptoethyltriethoxysilane (A-1893, Union Carbide) perform poorly in lowering the viscosities of magnesia compositions, the reaction products of the silanes with 1,2-butylene oxide are effective in lowering magnesia composition viscosities, which reaction products are comprised, respectively, of compounds believed to have the structures of formulae XIII and XIV:

(XIII)

A working parameter of solubility, $\delta_{wp}$, for a non-hydrolyzable moiety of each of the illustrated organo-silicon compounds may be derived by inserting the molar attraction and molar volume constants of Table I into expression II. A typical example of the calculation, as derived for the organo-silicon compound of formula XIV, would be as follows:

| Non-hydrolyzable moiety chemical groups | —CH₂— —CH₂— —S— —CH₂— —CH— —OH —CH₂— —CH₃ |
|---|---|
| ΣF | = 4(131.5) + 209.4 + 86.0 + 225.8 + 148.3 |
| | = 1195.5 |
| ΣV | = 4(21.8) + 21.6 + 13.6 + 14.9 + 27.8 |
| | = 165.1 |

-continued

| Non-hydrolyzable moiety chemical groups | $-CH_2-$ $-CH_2-$ $-S-$ $-CH_2-$ $-\overset{\mid}{CH}-$ $-OH$ $-CH_2-$ $-CH_3$ |
|---|---|
| $\delta_{wb} = \frac{\Sigma F}{\Sigma V}$ | $= \frac{1195.5}{165.1} = 7.24$ |

The working parameters of solubility for the other compounds depicted in the formulae III through XIII are derived as shown in the aforementioned example and listed in Table II. Experimental results as reported in the working examples which follow indicate a crucial range of working parameters of solubility values; within this range are included the depicted organo-silicon compounds that are known to provide improved castable, moldable, or sprayable cementitious magnesia compositions.

TABLE II

| Organo-Silicon Compound Structural Formula | Non-Hydrolyzable Moiety Working Parameter of Solubility, $\delta_{wp}$ (cal./cc.)$^{\frac{1}{2}}$ | Working Examples Relating to Preparation of Organo-Silicon Compound and/or Generation of Viscosity Data |
|---|---|---|
| VIII | 6.41 | VII |
| VII | 6.74 | VI |
| X | 6.95 | IX, X, IV |
| XI | 7.02 | IX, X, IV |
| III | 7.19 | I, II, III, IV, V |
| IX | 7.21 | IX, XIII |
| XIV | 7.24 | XII, XVI |
| V | 7.33 | XVII |
| IV | 7.36 | VIII |
| XIII | 7.43 | XI, XV |
| XII | 7.52 | XIII, XX |
| VI | 7.83 | XVIII |

It should be noted also that in utilization of the various organo-silicon compounds in magnesia compositions of the working examples, there is observed varying degrees of improvement in the casting, molding or spraying properties of cementitious magnesia compositions. The data derived from the working examples are reported in Table III, while the graphs of FIGS. I to VI illustrate viscosity profiles of preferred embodiments of the invention. "Improvement" is identified as a measurable net lowering of the viscosities of "test" magnesia compositions having the organo-silicon additive in comparison to changes in the viscosities of "control" magnesia compositions lacking the additive. Viscosity measurements are taken just after preparation of the compositions ("0 minutes") and at intervals on a Brookfield LVT viscometer equipped with a No. 4 spindle rotating at 12 r.p.m., with rotation of the spindle being maintained during the test period. Test magnesia compositions determined as providing improved properties are those which show a lower viscosity than the control at some initial measuring point and at one or more of the other measuring points during the test period.

Improvements in application properties of preferred magnesia compositions containing organo-silicon additives are demonstrated by the viscosity profile data of FIGS. 1-6. Some organo-silicon containing magnesia compositions show reduced viscosities for a short period of time, which reductions are followed by rather rapid increases in viscosity, such as shown by the composition of Example XIX B in FIG. 4. These sharp increases are believed attributable to some organo-silicon compounds exerting an accelerating effect on cure of the compositions. Magnesia compositions having short viscosity reduction periods would be useful in spraying applications where an initial viscosity reduction is beneficial in forcing the cementitious material through spray orifices, and where rapid setting of the sprayed material on a vertical substrate such as a wall is necessary to keep the material from sagging.

Figure 1:
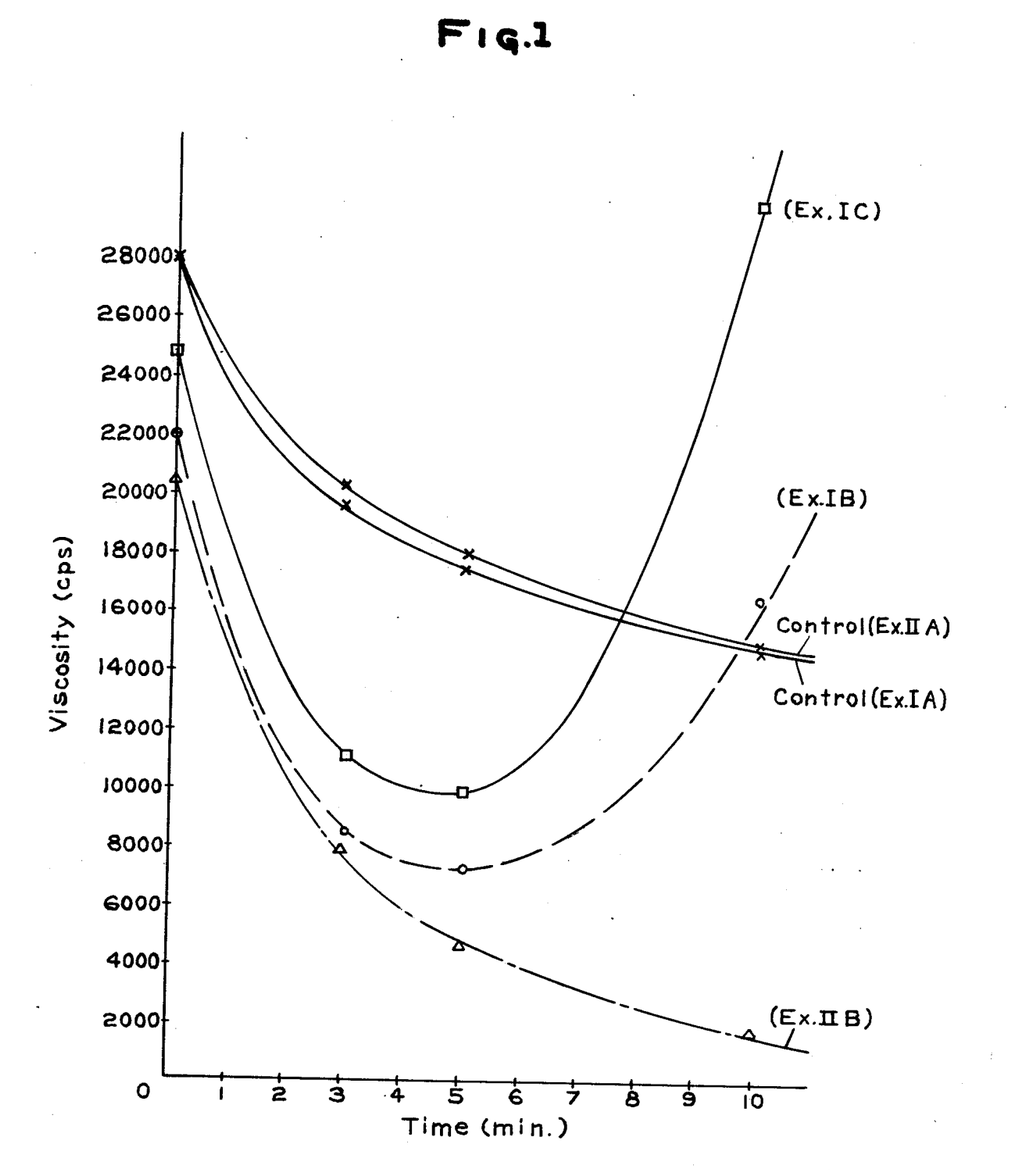
FIGS. 1 through 6 are graphs of viscosity profile data of preferred "test" compositions of the invention having an organo-silicon additive as compared against "control" compositions lacking the additive, illustrate examples of working embodiments of the invention according to the best mode so far devised in the practical application of the principles thereof.

On the other hand, some magnesia compositions containing the organo-silicon additive have viscosity reduction periods of ten minutes or more, such as shown by the composition of Example II B in FIG. 1. These compositions are quite useful for molding applications where it may be necessary to store a charge of the prepared, wet cementitious composition for some time before it is molded.

Cementitious magnesia compositions may have one or more of the described organo-silicon compounds in an amount in the range from about 0.5 percent to 10 percent or more by weight of the magnesium oxide in the composition. Preferably, the organo-silicon compounds are present in an amount in the range of about 2 to about 5 percent. A high percentage by weight of the organo-silicon component in the cementitious composition is generally not desirable because of the relatively high cost of the component.

The compositions are usually formulated by dissolving one or more water-soluble magnesium salts in an amount of water sufficient to form a saturated or nearly saturated water solution phase. Then in a separate vessel, such as a Patterson-Kelly mixer, organo-silicon compound is blended with the water-insoluble magnesium oxide to form a solid phase. The solid phase is then added to the magnesium salt-in-water solution with stirring to obtain a homogeneous slurry. It is also possible to add the organo-silicon compound, which is typically a liquid at room temperature, to a prepared slurry of the magnesium salt-in-water and magnesium oxide components.

The magnesia compositions are usable as described for casting articles in a mold form, with or without the use of compression or heat, and for spray applying onto a substrate. The compositions typically are in a slurry state when placed in the mold to form an article, and then the article is removed as soon as the composition cures sufficiently to a rigid state so that the molded article can be handled without any adverse effects. The cured article then will undergo an aging process with an increase in strength and hardness usually occurring.

It has been found that the compositions of the invention can be formulated in a two-package, storage stable system which in the presence of water forms a moldable and castable cementitious material of pourable consistency. The two-package system comprises a first composition which includes at least one magnesium salt having at least moderate solubility in water. A second composition of the two-package system is prepared from mixing together magnesium oxide and an organo-silicon compound of the type described above.

The first composition of the two-package system can comprise the magnesium salt, or salts, alone; or the first composition may have one or more magnesium salts of any of the aforementioned type dissolved in an amount of water effective to form a saturated or nearly saturated solution of the magnesium salt or salts. In either case, the first composition is sufficiently stable to satisfy most commercial or industrial storage conditions and shelf-life requirements.

The second composition is prepared by blending the organo-silicon compound in a Patterson-Kelly mixer as described above. It is believed any of the aforementioned organo-silicon compounds may be blended with magnesium oxide in the ratios set forth above and that these blends form stable compositions storable for lengths of time and under conditions typical for most of the contemplated uses.

Two-package systems for forming cementitious compositions of the invention are quite useful inasmuch as the blending of the magnesium oxide and organo-silicon components can be closely controlled by use of elaborate and expensive mixing equipment which may not be available to end users of the compositions. The two-package system has the further advantage of requiring only one mixing step by the ultimate user which thereby enhances the convenience of use of the compositions and ensures the optimum ratio of components in the material for molding, casting or spraying uses.

Quite often, magnesia compositions of the described formulations contain additional materials to increase the cure rate, to increase wet or dry strength, to reduce shrinkage, to prevent cracking or to reduce water sensitivity of the cured composition.

Additives to increase the wet strength or to improve the strength or crack resistance of the cured composition include materials such as fibrous glass, sisal, mineral wool, mica and cotton, each of which may be present in mat or chopped form. Typically, these materials are present in an amount in a range from about 1 to about 50 percent by weight of the cured composition and preferably from about 5 to about 30 percent.

There may be surfactants present in the cementitious compositions to improve spreadability of the compositions in the wet form. Examples of such additives include non-ionic surfactants which may be present in an amount sufficient to reduce the surface tension of the uncured composition; usually surfactants are present in an amount in a range from about 0.1 to about 5 percent by weight of the wet composition.

Other useful additives which may be included in the magnesia compositions, especially for compositions utilized for molding purposes, are thickening agents, fillers and mold release agents. Thickening agents which serve to maintain uniform consistency in the wet composition matrix include hydroxyethyl cellulose, hydroxypropyl cellulose, polyethylene oxide and polyvinyl alcohol. Examples of fillers are clays, talc and calcium carbonate. Suitable mold release agents include "Zelec UN" (DuPont), zinc stearate, aluminum stearate and various lubricating silicone compounds. When used, these additives may be present in an amount in the range of about 0.01 to about 5 weight percent based on total weight of the wet composition.

Coloring pigments or water-soluble dyes may also be present in the compositions. Typical coloring pigments include iron oxides, cadmium sulphide, carbon black, phthalocyanine blue, phthalocyanine green, ultramarine blue, chromium oxide, burnt umber, benzidine yellow, toluidine red and aluminum powder. When used, pigments may be present in an amount in the range of about 0.1 to about 10 weight percent based on total weight of the wet composition.

When any of the aforementioned additives are to be included in the cementitious compositions, the additives may be introduced during any one of the composition preparation stages, or may be included in either of the compositions of the two-package system.

The following examples set forth specific embodiments of the invention. However, the invention is not to be construed as being limited to these embodiments for there are, of course, numerous possible variations and modifications. All parts and percentages of the examples as well as throughout the specification are by weight unless otherwise indicated.

EXAMPLE I

Into a mixing vessel there is charged 40.0 parts water together with 68.8 parts magnesium chloride hexahydrate. Mixing proceeds until the magnesium chloride compound is completely dissolved in the water. Then 102 parts magnesium oxide is added to the vessel and mixing proceeds just long enough to obtain a smooth uniform blend, with care being taken so that excessive heat is not generated. A portion of the composition is then immediately placed into a Brookfield LVT viscometer vessel equipped with a No. 4 spindle rotated at 12 r.p.m. Viscosity readings on this composition "A", designated as "control", are taken at regular intervals until curing of the composition gives noticeably increasing viscosity values.

A second composition designated as composition "B", is prepared precisely as set forth above for composition "A" as to reactants and mixing procedure, except that near the end of the magnesium oxide blending step 3.4 parts γ-aminopropyltriethoxysilane viscosity reducing agent is added to the mixture. Viscosity readings are taken immediately on a sample of composition "B" as set forth above.

A third composition, designated as composition "C", is prepared according to the reactants and mixing procedure for composition "B", except that 2.1 parts completely -aminopropyltriethoxysilane is added to the mixture near the end of the magnesium oxide blending step. Comparative viscosity data are listed in Table III and illustrated in FIG. 1.

EXAMPLE II

Into a mixer there are charged 20 parts water, 34.4 parts magnesium chloride hexahydrate and 51 parts magnesium oxide in the order and according to the mixing procedure set forth in Example I to make a control composition "A". Similarly, test composition "B" is prepared as "A" with the addition of 1.68 parts γ-aminopropyltriethoxysilane as a viscosity reducing agent. Viscosity readings taken as before are listed in Table III and displayed in FIG. 1.

EXAMPLE III

Using the procedure of Example I, a control composition "A" is prepared from 26.1 parts water, 36.3 parts magnesium acetate tetrahydrate and 51 parts magnesium oxide. Similarly, a test composition "B" is prepared as "A" with the addition of 1.68 parts γ-aminopropyltriethoxysilane. Table III lists data of comparative viscosity readings taken of the compositions.

EXAMPLE IV

Using the procedure of Example I, a control composition "A" is prepared from 20 parts water, 49.5 parts magnesium bromide hexahydrate and 51 parts magnesium oxide. A test composition "B" is prepared like composition "A" with the further addition of 1.68 parts of γ-aminopropyltriethoxysilane. Table III lists comparative viscosity data of the compositions.

EXAMPLE V

Using the procedure of Example I, a control composition "A" is prepared from 20 parts water, 43.4 parts magnesium nitrate hexahydrate and 51 parts magnesium oxide. A test composition "B" is prepared like composition "A" with the further addition of 1.68 parts of γ-aminopropyltriethoxysilane. Table III lists comparative viscosity data of the compositions.

EXAMPLE VI

Figure 2:
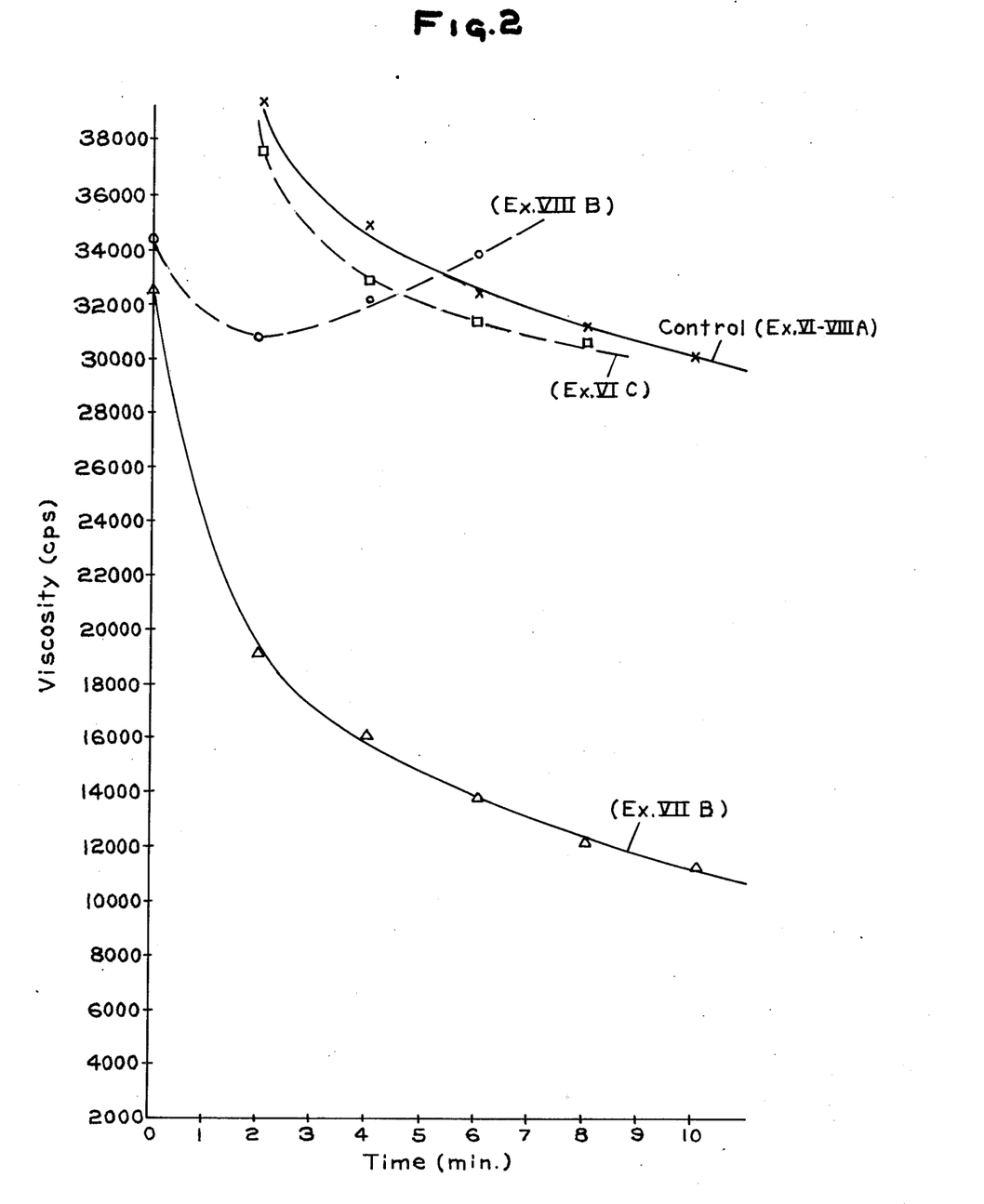
Figure 3:
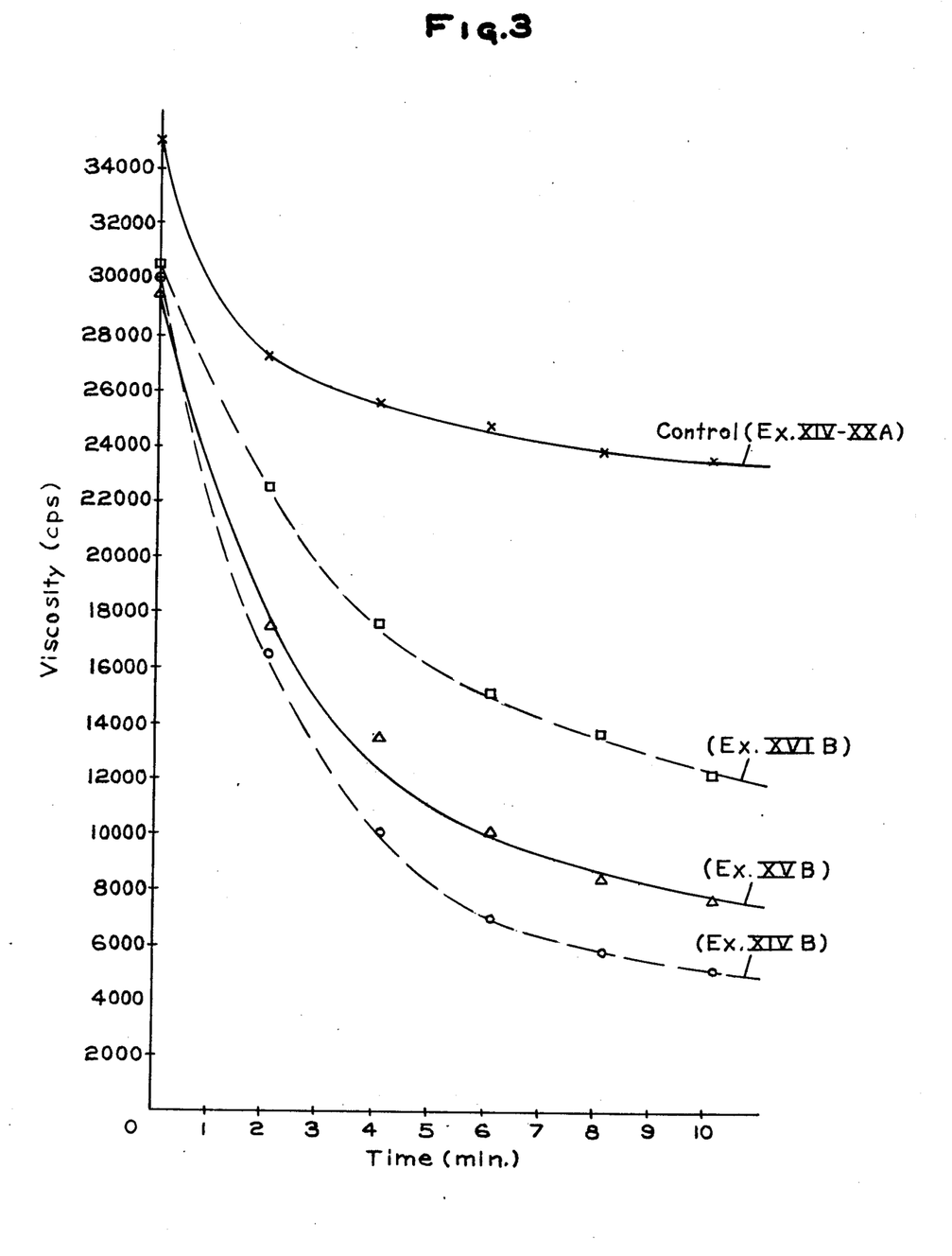
Figure 4:
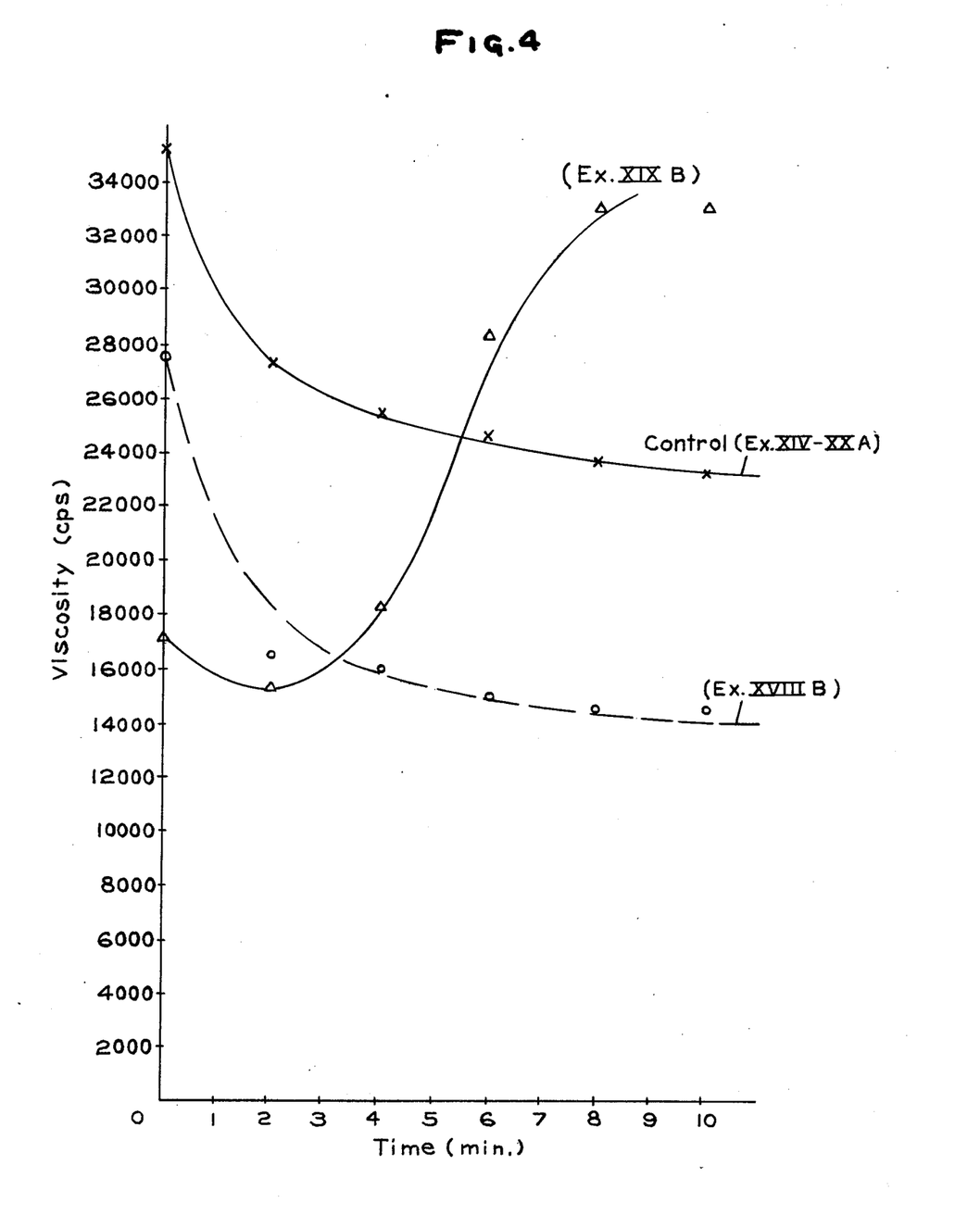
Figure 5:
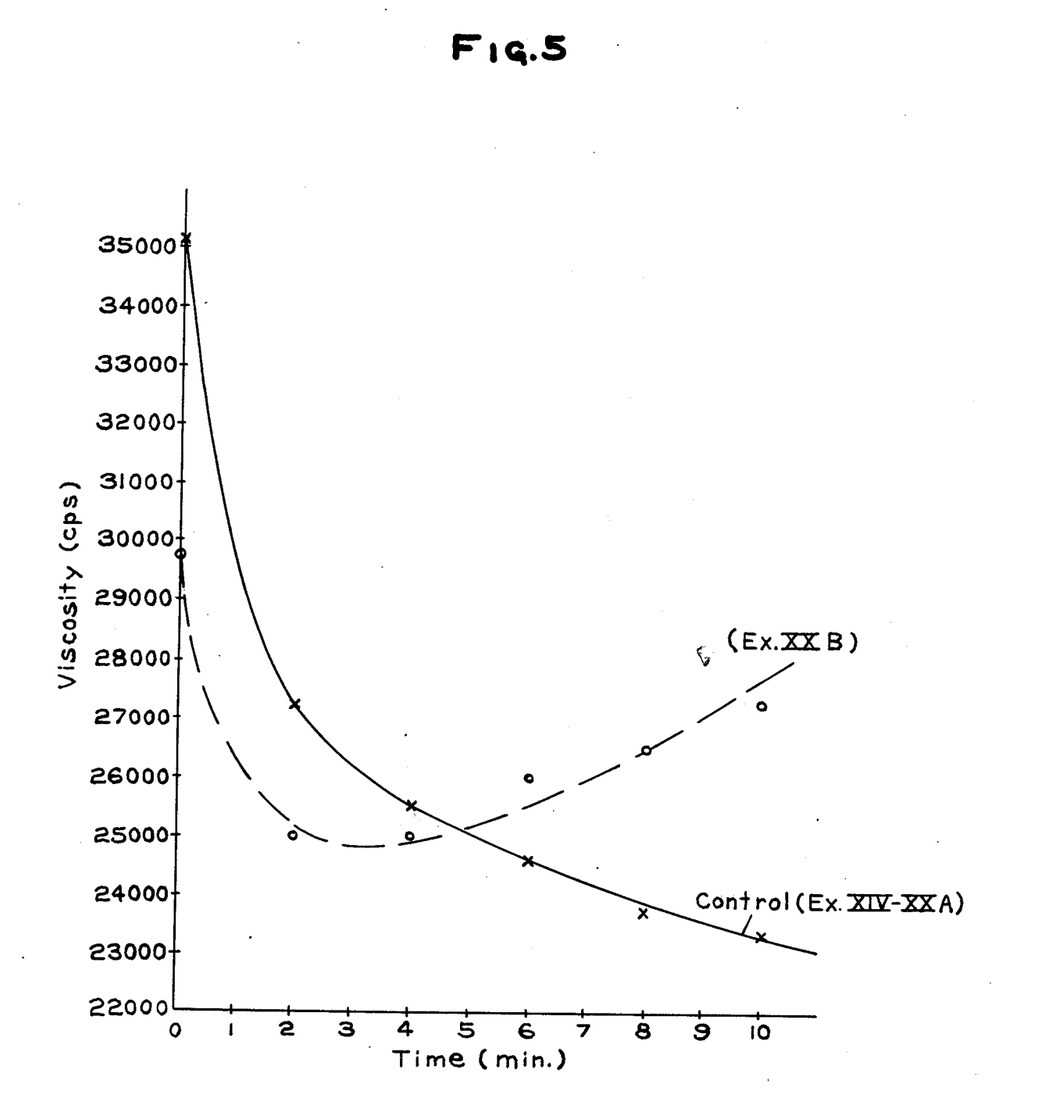
Figure 6:
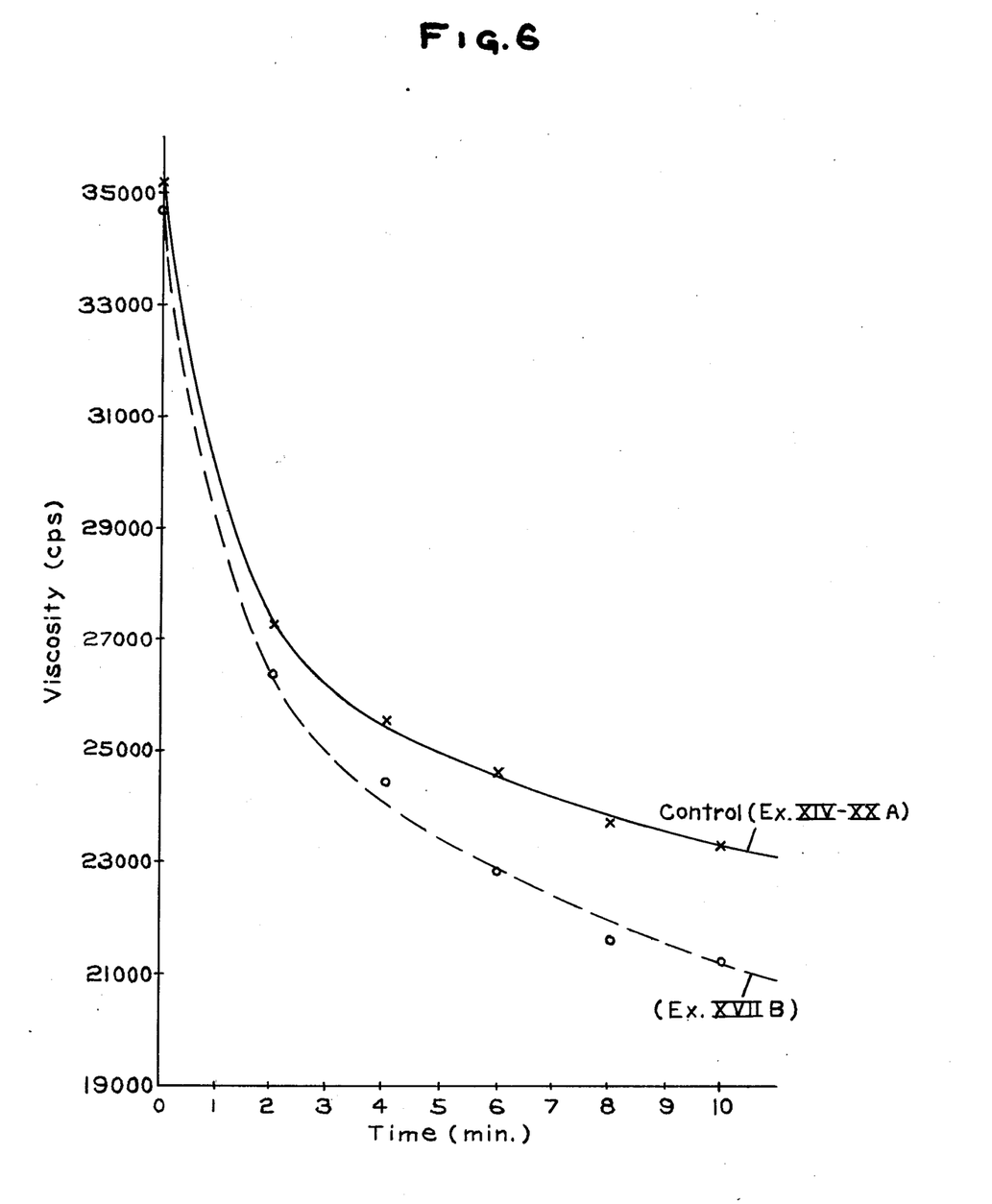

Into a mixing vessel there is charged 40.0 parts water together with 68.8 parts magnesium chloride hexahydrate. Mixing proceeds until the magnesium chloride is completely dissolved in the water. Then 102 parts magnesium oxide is added to the vessel and mixing proceeds just long enough to obtain a smooth uniform blend, with care being taken so that excessive heat is not generated. A portion of the composition is then immediately placed into a Brookfield LVT viscometer vessel equipped with a No. 4 spindle rotated at 12 r.p.m. Viscosity readings on this composition "A", designated as "control", are taken at regular intervals until curing of the composition gives noticeably increasing viscosity values. Test composition "B" and "C" are prepared like composition "A" with the further addition of 3.2 parts γ-aminopropylmethyldiethoxysilane to each of the test compositions near the end of the magnesium oxide blending step. Table III shows comparative viscosity data of the composition. FIG. 2 shows a graphic comparison of the viscosity profiles of compositions "A" and "C".

EXAMPLE VII

A test composition "B" is prepared according to the procedure of Example VI except that the amino silane additive consists of 3.2 parts δ-aminobutyldimethylmethoxysilane. Viscosity test data shown in Table III and FIG. 2 are compared against control data of Example VI.

EXAMPLE VIII

A test composition "B" is prepared by introducing 102 parts magnesium oxide into a Patterson-Kelly blender equipped with a liquid feed device in the intensifier bar. Through the liquid feed device there is charged 3.2 parts N-β-aminoethyl-γ-aminopropyltrimethoxysilane to form a pre-mix "dry" blend. Mixing continues until a homogeneous blend is obtained. In a mixing vessel there is charged 68.8 parts magnesium chloride hexahydrate together with 40.0 parts water. Mixing proceeds to achieve a homogeneous solution. Then the dry blend is added to the previously prepared magnesium chloride-in-water solution with mixing sufficient to obtain a homogeneous blend. Viscosity data, reported in Table III and illustrated in FIG. 2, are compared against control data of Example VI.

EXAMPLE IX

Into a reaction vessel equipped with agitating and heating means, a thermometer and a reflux condenser, there is charged a solution comprising 44.2 parts γ-aminopropyltriethoxysilane and 79.6 parts ethanol. The solution is heated to about 40° C. and then 15.4 parts 1,2-butylene oxide is added to the solution over a period of 30 minutes. The reaction mixture is heated to a reflux temperature of about 78° C., with the reaction mixture being maintained under refluxing conditions for an additional four hours, after which time the mixture is allowed to cool to room temperature. Analysis of the reaction product shows that about 76 percent of the product is an organo-silicon compound containing a secondary amine group, believed to have the structure of formulae IX or XI, and about 23 percent of the product is an organo-silicon compound containing a tertiary amino group believed to have the structure of formula X.

EXAMPLE X

Into a reaction vessel equipped as in Example IX, there is charged a solution comprising 44.2 parts γ-aminopropyltriethoxysilane and 74.6 parts ethanol. The solution is heated to about 40° C. and then 30.4 parts 1,2-butylene oxide is added to the solution over a period of 30 minutes. The reaction mixture is heated to a reflux temperature of about 78° C., with the reaction mixture being maintained under refluxing conditions for an additional four hours, after which time the mixture is allowed to cool to room temperature. Analysis of the reaction product shows that about 87 percent of the product is an organo-silicon compound containing a tertiary amino group, which compound is believed to have the structure of formula X.

EXAMPLE XI

Into a reaction vessel equipped as in Example IX, there is charged 105.6 parts of a 50 percent solution of ureidopropyltriethoxysilane in methanol. The solution is heated to about 40° C. and then 15.2 parts 1,2-butylene oxide is added to the solution over a period of 30 minutes. The reaction mixture is heated to a reflux temperature of about 65° C., with the reaction mixture being maintained under refluxing conditions for an additional four hours, after which time the mixture is allowed to cool to room temperature. The reaction product is believed to comprise chiefly an organo-silicon compound containing a urea group, which compound is believed to have the structure of formula XIII.

EXAMPLE XII

Into a reaction vessel equipped as in Example IX, there is charged a solution comprising 48.8 parts mercaptoethyltriethoxysilane and 70.0 parts ethanol. The solution is heated to about 40° C. and then 15.2 parts 1,2-butylene oxide is added to the solution over a period of 30 minutes. The reaction mixture is heated to a reflux temperature of about 78° C., with the reaction mixture being maintained under refluxing conditions for an additional four hours, after which time the mixture is allowed to cool to room temperature. Analysis of the reaction product shows substantially no unreacted epoxide groups. The reaction product is believed to comprise chiefly an organo-silicon compound containing a fully-substituted thio group, which compound is believed to have the structure of formula XIV. EXAMPLE XIII Into a reaction vessel equipped as in Example IX, there is charged a solution comprising of 66.3 parts γ-aminopropyltriethoxysilane and 81.6 parts ethanol to which is then added 5.1 parts 1,4-butanediol diglycidyl ether. The reaction mixture is heated to about 40° C. and then 10.1 parts more 1,4-butanediol diglycidyl ether is added dropwise to the reaction mixture over a period of about 30 minutes. Then the reaction mixture is maintained at a refluxing temperature for an additional 30 minutes. Analysis of the reaction product shows substantially no unreacted epoxide group.

EXAMPLE XIV

Using the procedure of Example I, three control compositions "A" are prepared from 40.0 parts water, 68.8 parts magnesium chloride hexahydrate and 102 parts magnesium oxide. A fourth control composition "A" is prepared like the other three control compositions with the further addition of 1.5 percent ethanol by weight of the wet composition; the control composition containing ethanol is prepared for the detection of background effects of the ethanol solvent in which some of the organo-silicon compounds are dissolved in preparation of the test compositions. The control compositions "A" show fairly consistent behavior during the viscosity measuring period, with the presence of ethanol in one of the control compositions being observed to have little effect on the behavior of the composition as compared to the other control compositions. Hence, viscosity data is averaged to give a single range of values as reported in Table III and as shown in FIGS. 3–6.

A test composition "B" is prepared as in Example I from 40.0 parts water, 68.8 parts magnesium chloride hexahydrate and 102 parts magnesium oxide with the addition near the end of the magnesium oxide blending step of 7.37 parts of the organo-silicon compound reaction product prepared as in Example IX. Viscosity data is shown in Table III and FIG. 3.

EXAMPLE XV

A test composition "B" is prepared as in Example XIV, except that the organo-silicon additive consists of 7.37 parts of the reaction product prepared as in Example X. Viscosity data is shown in Table III and FIG. 3.

EXAMPLE XVI

A test composition "B" is prepared as in Example XIV, except that the organo-silicon additive consists of 7.37 parts of the reaction product prepared as in Example XI. Viscosity data is shown in Table III and FIG. 3.

EXAMPLE XVII

Three test compositions "B" are prepared as in Example XIV, except that the organo-silicon additive for each composition consists of 7.4 parts of the reaction product prepared as in Example XII. Viscosity data is shown in Table III and FIG. 6.

EXAMPLE XVIII

A test composition "B" is prepared as in Example XIV, except that the organo-silicon additive comprises 3.4 parts of a compound having the structure depicted in formula V. Viscosity data are shown in Table III and FIG. 4.

EXAMPLE XIX

A test composition "B" is prepared as in Example XIV, except that the organo-silicon compound comprises 3.4 parts of a compound having the structure depicted in formula VI. Viscosity data are shown in Table III and FIG. 4.

EXAMPLE XX

A test composition "B" is prepared as in Example XIV, except that the organo-silicon additive comprises 7.37 parts of the reaction product prepared as in Example XIII. Viscosity data are shown in Table III and FIG. 5.

TABLE III

| Example No. | Viscosity Readings (× 1000 cps.) | | | | | | | | |
|---|---|---|---|---|---|---|---|---|---|
| | 0 min. | 1 min. | 2 min. | 3 min. | 4 min. | 5 min. | 6 min. | 8 min. | 10 min. |
| I A | 28.0 | | | 19.8 | | 17.5 | | | 14.8 |
| B | 22.0 | | | 8.5 | | 7.4 | | | 16.7 |
| C | 25.0 | | | 11.0 | | 10.0 | | | 30.3 |
| II A | 28.0 | | | 20.3 | | 18.0 | | | 14.5 |
| B | 20.5 | | | 8.0 | | 4.8 | | | 1.8 |
| III A | 150.0 | | | 136.0 | | 127.0 | | | 101.0 |
| B | 130.0 | | | 77.0 | | 60.0 | | | 37.6 |
| IV A | 16.0* | | | 20.5 | | 19.3 | | | 18.0 |
| B | 7.2 | | | 1.7 | | 1.1 | | | 2.5 |
| V A | 9.3 | | | 4.8 | | 4.1 | | | 3.5 |
| B | 4.4 | | | 1.8 | | 0.95 | | | 1.2 |
| VI-VIII A | 38.0 | 42.5 | 39.3 | | 34.8 | | 32.3 | 31.0 | 29.8 |
| VI B | 35.0 | 39.3 | 36.5 | | 32.3 | | 31.3 | 30.5 | |
| C | 48.0 | 43.0 | 38.0 | | 32.3 | | 31.5 | 30.6 | |
| VII B | 32.5 | | 19.2 | | 16.0 | | 13.8 | 12.0 | 11.0 |
| VIII B | 34.3 | | 30.5 | | 32.0 | | 33.8 | | |
| XIV-XX A** | 35.2 | | 27.2 | | 25.5 | | 24.6 | 23.7 | 23.3 |
| XIV B | 30.0 | | 16.5 | | 10.0 | | 6.9 | 5.7 | 5.0 |
| XV B | 29.5 | | 17.5 | | 13.5 | | 10.0 | 8.3 | 7.5 |
| XVI B | 30.5 | | 22.5 | | 17.5 | | 15.0 | 13.5 | 12.0 |
| XVII B*** | 34.7 | | 26.4 | | 24.4 | | 22.8 | 21.6 | 21.2 |
| XVIII B | 27.5 | | 16.5 | | 16.0 | | 15.0 | 14.5 | 14.5 |
| XIX B | 17.0 | | 15.3 | | 18.3 | | 28.5 | 33.0 | 33.0 |

TABLE III-continued

| Example No. | Viscosity Readings (× 1000 cps.) | | | | | | | | |
|---|---|---|---|---|---|---|---|---|---|
| | 0 min. | 1 min. | 2 min. | 3 min. | 4 min. | 5 min. | 6 min. | 8 min. | 10 min. |
| XX B | 29.8 | | 25.0 | | 25.0 | | 26.0 | 26.5 | 27.3 |

*Value is unreliable because of erratic operation of test apparatus.
**Average of four samples.
***Average of three samples.

EXAMPLE XXI

Into a mixing vessel there is charged 186 parts water, together with 320 parts magnesium chloride hexahydrate. With continuous mixing at moderate speed there is gradually added to the vessel 5.8 parts hydroxyethyl cellulose. Mixing continues until a thoroughly homogeneous solution is obtained, after which time this "liquid phase" is allowed to age for several hours.

Into a Patterson-Kelly blender equipped with a liquid feed device in the intensifier bar, there is charged 449 parts magnesium oxide. Through the liquid feed device there is charged 16 parts γ-aminopropyltriethoxysilane viscosity reducing agent. Mixing is continued until a homogeneous blend is obtained. Then 23 parts of a polyvinyl chloride resin is added to the vessel, followed by continuous mixing to obtain a uniform mixture known as a "dry blend".

A wet molding composition to be used immediately is prepared by bringing together 488 parts of the dry blend and 512 parts of the liquid phase. Mixing proceeds vigorously for as short a period of time as possible to obtain a composition having a smooth, creamy consistency. Into a mold designed to form a panel six inches square and about 0.1 inch thick, there are placed a one-ply layer of commercially available finely-spun fiberglass veil mat, a continuous-strand fiberglass mat, a charge of the wet molding composition sufficient to fill the mold and an overlay of one-ply fiberglass veil mat. The mold parts are closed, a mold compressive force of 100 psi is applied and a mold temperature of 127°–132° C. is maintained for about two minutes. The mold is opened and an acceptably cured panel is removed that is observed to have a hard surface upon handling.

EXAMPLE XXII

Into a mixing vessel there is charged 186 parts water, together with 320 parts magnesium chloride hexahydrate. With continuous mixing at moderate speed there is gradually added to the vessel 5.8 parts hydroxyethyl cellulose. Mixing continues until a thoroughly homogeneous solution is obtained, after which time this "liquid phase" is allowed to age for several hours.

Into a Patterson-Kelly blender equipped with a liquid feed device in the intensifier bar, there is charged 3580 parts magnesium oxide. Through the liquid feed device there is charged 118.1 parts γ-aminopropyltriethoxysilane viscosity reducing agent. Mixing is continued until a homogeneous "dry" blend is obtained.

A wet molding composition to be used immediately is prepared by bringing together 116 parts of the dry blend and 128.2 parts of the liquid phase. Mixing proceeds vigorously for as short a period of time as possible to obtain a composition having a smooth, creamy consistency. Into a mold designed to form a panel six inches square and about 0.1 inch thick, there are placed a one-ply layer of commercially available finely-spun fiberglass veil mat, two piles of a continuous strand fiberglass mat, a charge of the wet molding composition sufficient to fill the mold and an overlay of one-ply fiberglass veil mat. The mold parts are closed, a mold compressive force of 100 psi is applied and a mold temperature of 121°–127° C. is maintained for about three minutes. The mold is opened and an acceptably cured panel is removed that is observed to have a hard surface upon handling.

EXAMPLE XXIII

Into a mixing vessel there is charged 186 parts water, together with 320 parts magnesium chloride hexahydrate. With continuous mixing at moderate speed there is gradually added to the vessel 5.8 parts hydroxyethyl cellulose. Mixing continues until a thoroughly homogeneous solution is obtained.

Into a Patterson-Kelly blender equipped with a liquid feed device in the intensifier bar, there is charged 3580 parts magnesium oxide. Through the liquid feed device there is charged 118.1 parts γ-aminopropyltriethoxysilane viscosity reducing agent. Mixing is continued until a homogeneous "dry" blend is obtained.

A wet molding composition to be used immediately is prepared by bringing together 116 parts of the dry blend, 128.2 parts of the liquid phase and 12.0 parts polyethylene powder. Mixing proceeds vigorously for as short a period of time as possible to obtain a composition having a smooth, creamy consistency. Into a mold designed to form a panel six inches square and about 0.1 inch thick, there are placed a one-ply layer of commercially available finely-spun fiberglass veil mat, two plies of a continuous strand fiberglass mat, a charge of the wet molding composition sufficient to fill the mold and an overlay of one-ply fiberglass veil mat. The mold parts are closed, a mold compressive force of 100 psi is applied and a mold temperature of 121°–127° C. is maintained for about three minutes. The mold is opened and an acceptably cured panel is removed that is observed to have a hard surface upon handling.

Although specific examples of the instant invention have been set forth hereinabove, it is not intended that the invention be limited solely thereto, but is to include all the variations and modifications falling within the scope of the appended claims.

What is claimed is:

1. A moldable, castable or sprayable cementitious composition, comprising:
   (a) magnesium oxide;
   (b) a magnesium salt having at least moderate solubility in water;
   (c) at least one organo-silicon compound, characterized in having attached to the silicon atom (i) at least one group having a hydrolyzable bond with the silicon atom and selected from the group consisting of halogen, hydroxyl, alkoxyl, aryloxyl, substituted aryloxyl, aralkoxyl, substituted aralkoxyl, alkylamino, substituted alkylamino, silylamino, substituted silylamino, mercapto and substituted mercapto and (ii) at least one moiety attached through a substantially non-hydrolyzable silicon-carbon bond, wherein the moiety has a working parameter of solubility, $\delta_{wp}$, in the range of about 6.2 to about 8.0 (cal./c.c.)$^{\frac{1}{2}}$, with $$\delta_{wp} = \frac{\Sigma F_i}{\Sigma V_i}$$

wherein:
$F_i$=the molar attraction constant of an individual functional group of said moiety expressed in (cal. c.c.)$^{\frac{1}{2}}$ per mole, and
$V_i$=the molar volume constant of an individual group of said moiety expressed in c.c. per mole; and (d) a liquid phase comprising water;
wherein the mole ratio of the magnesium oxide to the magnesium salt ranges from 3:1 to 10:1, the level of organo-silicon compound ranges from about 0.5 percent to 10 percent by weight of the magnesium oxide and the water is in an amount effective to cause reaction of at least a portion of said magnesium oxide and at least a portion of said magnesium salt to form a matrix curable to a hardened state.

2. The cementitious composition of claim 1, wherein said magnesium salt is selected from the group consisting of magnesium chloride, hydrated magnesium chloride, hydrated magnesium sulphate, hydrated magnesium nitrate, hydrated magnesium acetate, magnesium bromide and hydrated magnesium bromide.

3. The cementitious composition of claim 1, wherein said organo-silicon compound moiety comprises alkyl or oxalkyl group which may be substituted with one or more groups selected from the group consisting of alkyl, alkoxy, aryl, aryloxy, substituted aryloxy, acrylyl, substituted acrylyl, carbohydroxy, carboalkoxy, amino, amido, ureido, epoxy and sulphur.

4. The cementitious composition of claim 3, wherein said organo-silicon compound is a reaction product of a compound containing acrylyl or substituted acrylyl groups and a silane having a non-hydrolyzable moiety comprising an amino group containing at least one active hydrogen.

5. The cementitious composition of claim 3, wherein said organo-silicon compound is a reaction product of an amino-compound having at least one active hydrogen and a silane having a non-hydrolyzable moiety comprising acrylyl or substituted acrylyl groups.

6. The cementitious composition of claim 3, wherein said organo-silicon compound is a reaction product of a silane having a non-hydrolyzable moiety containing an epoxy group and a compound containing a chemical group selected from the group consisting of amino, amide, ureido, urea, urethane, thiol and hydroxyl, each having at least one active hydrogen atom.

7. The cementitious composition of claim 3, wherein said organo-silicon compound is a reaction product of an epoxy-containing compound and a silane having a non-hydrolyzable moiety comprising one or more chemical groups selected from the group consisting of primary amino, secondary amino, amide, ureido, urea, urethane and thiol, each having at least one active hydrogen atom.

8. The cementitious composition of claim 7, wherein said epoxy-containing compound is an aliphatic epoxide and said silane is an aminoalkylsilane.

9. The cementitious composition of claim 8, wherein said aliphatic epoxide is 1,2-butylene oxide and said aminoalkylsilane is γ-aminopropyltriethoxysilane.

10. The cementitious composition of claim 7, wherein said aliphatic epoxide is 1,2-butylene oxide and said silane is ureidopropyltriethoxysilane.

11. The cementitious composition of claim 7, wherein said epoxy-containing compound is an aliphatic epoxide and said silane is a thioalkylsilane.

12. The cementitious composition of claim 11, wherein said aliphatic epoxide is 1,2-butylene oxide and said thioalkylsilane is mercaptoethyltriethoxysilane.

13. The cementitious composition of claim 7, wherein said epoxy-containing compound is an aliphatic polyepoxide and said silane is an aminoalkylsilane.

14. The cementitious composition of claim 13, wherein said aliphatic polyepoxide is 1,4-butanediol diglycidyl ether and said aminoalkylsilane is γ-aminopropyltriethoxysilane.

15. The cementitious composition of claim 1, wherein said organo-silicon compound has the structure:

16. The cementitious composition of claim 1, wherein said organo-silicon compound has the structure:

17. The cementitious composition of claim 1, wherein said organo-silicon compound has the structure:

18. The cementitious composition of claim 1, wherein said organo-silicon compound has the structure:

19. The cementitious composition of claim 1, wherein said organo-silicon compound has the structure:

20. The cementitious composition of claim 1, wherein said organo-silicon compound has the structure:

21. The cementitious composition of claim 1 further comprising a material selected from the group consisting of fibrous glass, sisal, mica, mineral wool and the cotton.

22. The cementitious composition of claim 1 further comprising a thickening agent selected from the group consisting of hydroxyethyl cellulose, hydroxypropyl cellulose, polyethylene oxide and polyvinyl alcohol.

23. The cementitious composition of claim 1 wherein the mole ratio of the magnesium oxide to the magnesium salt ranges from 6:1 to 7.5:1 and the level of organo-silicon compound in the composition ranges from about 2 percent to about 5 percent by weight of the magnesium oxide.

24. A process for forming an article from a curable cementitious composition, comprising:
 (a) mixing together in the presence of a liquid phase having water sufficient to produce a moldable, curable slurry composition from the components of:
   (1) magnesium oxide;
   (2) at least one magnesium salt having moderate solubility in water; and
   (3) at least one organo-silicon compound, characterized in having attached to the silicon atom (i) at least one group having a hydrolyzable bond with the silicon atom and selected from the group consisting of halogen, hydroxyl, alkoxyl, aryloxyl, substituted aryloxyl, aralkoxyl, substituted aralkoxyl, alkylamino, substituted alkylamino, silylamino, substituted silylamino, mercapto and substituted mercapto and (ii) at least one moiety attached through a substantially non-hydrolyzable silicon-carbon bond, wherein the moiety has a working parameter of solubility, $\delta_{wp}$, in the range of about 6.2 to about 8.0 (cal./c.c.)$^{\frac{1}{2}}$, with $$\delta_{wp} = \frac{\Sigma F_i}{\Sigma V_i}$$

wherein:
$F_i$ = the molar attraction constant of an individual functional group of said moiety expressed in (cal. c.c.)$^{\frac{1}{2}}$ per mole, and
$V_i$ = the molar volume constant of an individual group of said moiety expressed in c.c. per mole
wherein the mole ratio of the magnesium oxide to the magnesium salt ranges from 3:1 to 10:1 and the level of organo-silicon compound ranges from about 0.5 percent to 10 percent by weight of the magnesium oxide
 (b) placing said slurry composition in a mold form; and
 (c) allowing said composition to cure sufficiently such that said article may be removed from the mold form without substantially adversely affecting the integrity of the molded article.

25. The process of claim 24, wherein said components are mixed together by
 (a) firstly, preparing a blend of said magnesium oxide and said organo-silicon compound; and
 (b) subsequently mixing said blend with said magnesium salt in the presence of said water.

26. The process of claim 24 further comprising introducing into said slurry composition a material selected from the group consisting of fibrous glass, sisal, silicas, mica, mineral wool and cotton.

27. The process of claim 24 further comprising forming said article with the aid of compression force or heat, or both.

28. The process of claim 24, wherein said magnesium salt is selected from the group consisting of magnesium chloride, hydrated magnesium chloride, hydrated magnesium sulphate, hydrated magnesium nitrate, hydrated magnesium acetate, magnesium bromide and hydrated magnesium bromide.

29. The process of claim 24, wherein said organo-silicon compound moiety comprises alkyl or oxalkyl group which may be substituted with one or more groups selected from the group consisting of alkyl, alkoxy, aryl, aryloxy, substituted aryloxy, acrylyl, substituted acrylyl, carbohydroxy, carboalkoxy, amino, amido, ureido, epoxy and sulphur.

30. The process of claim 29, wherein said organo-silicon compound is a reaction product of a compound containing acrylyl or substituted acrylyl groups and a silane having a non-hydrolyzable moiety comprising an amino group containing at least one active hydrogen atom.

31. The process of claim 29, wherein said organo-silicon compound is a reaction product of an amino-compound having at least one active hydrogen and a silane having a non-hydrolyzable moiety comprising acrylyl or substituted acrylyl groups.

32. The process of claim 29, wherein said organo-silicon compound is a reaction product of a silane having a non-hydrolyzable moiety containing an epoxy group and a compound containing a chemical group selected from the group consisting of amino, amide, ureido, urea, urethane, thiol, and hydroxyl, each having at least one active hydrogen atom.

33. The process of claim 29, wherein said organo-silicon compound is a reaction product of an epoxy-containing compound and a silane having a non-hydrolyzable moiety comprising one or more chemical groups selected from the group consisting of primary amino, secondary amino, amide, urea, urethane, ureido and thiol, each having at least one active hydrogen atom.

34. The process of claim 33, wherein said epoxy-containing compound is an aliphatic epoxide and said silane is an aminoalkylsilane.

35. The process of claim 24, wherein said organo-silicon compound is selected from the group consisting of compounds illustrated by the formulae:

(a)

(b)

(c)

(d)

(e)

-continued

36. The process of claim 24, wherein said organo-silicon compound is a reaction product selected from the group consisting of
   (a) a reaction product of 1,2-butylene oxide and γ-aminopropyltriethoxysilane;
   (b) a reaction product of 1,2-butylene oxide and ureidopropyltriethoxysilane;
   (c) a reaction product of 1,2-butylene oxide and mercaptoethyltriethoxysilane; and
   (d) a reaction product of 1,4-butanediol diglycidyl ether and γ-aminopropyltriethoxysilane.

37. The process of claim 24 wherein the level of the magnesium oxide to the magnesium salt ranges from 6:1 to 7.5:1 and the level of the organo-silicon compound ranges from about 2 percent to about 5 percent by weight of the magnesium oxide.

38. A product produced by the process of claim 24.

39. A storage stable two-package system for forming in the presence of water a moldable, castable or sprayable cementitious material when a first composition is mixed with a second composition, comprising:
   (a) said first composition including at least one magnesium salt having at least moderate solubility in water; and
   (b) said second composition prepared from mixing together
      (1) magnesium oxide; and
      (2) at least one organo-silicon compound, characterized in having attached to the silicon atom (i) at least one group having a hydrolyzable bond with the silicon atom and selected from the group consisting of halogen, hydroxyl, alkoxyl, aryloxyl, substituted aryloxyl, aralkoxyl, substituted aralkoxyl, alkylamino, substituted alkylamino, silylamino, substituted silylamino, mercapto and substituted mercapto and (ii) at least one moiety attached through a substantially non-hydrolyzable silicon-carbon bond, wherein the moiety has a working parameter of solubility, $\delta_{wp}$, in the range of about 6.2 to about 8.0 (cal./c.c.)$^{\frac{1}{2}}$, with $$\delta_{wp} = \frac{\Sigma F_i}{\Sigma V_i}$$

wherein:
   $F_i$=the molar attraction constant of an individual functional group of said moiety expressed in (cal. c.c.)$^{\frac{1}{2}}$ per mole, and
   $V_i$=the molar volume constant of an individual group of said moiety expressed in c.c. per mole with the organo-silicon compound at a level ranging from about 0.5 percent to 10 percent by weight of th magnesium oxide 40. The two-package system of claim 39, wherein said first composition further comprises water in an amount effective to form a saturated or nearly saturated solution with said magnesium salt.

41. The two-package system of claim 39, wherein said magnesium salt is selected from the group consisting of magnesium chloride, hydrated magnesium chloride, hydrated magnesium sulphate, hydrated magnesium nitrate, hydrated magnesium acetate, magnesium bromide and hydrated magnesium bromide.

42. The two-package system of claim 39, wherein said organo-silicon compound moiety comprises alkyl or oxalkyl group which may be substituted with one or more groups selected from the group consisting of alkyl, alkoxy, aryl, aryloxy, substituted aryloxy, acrylyl, substituted acrylyl, carbohydroxy, carboalkoxy, amino, amido, ureido, epoxy and sulphur.

43. The two-package system of claim 42, wherein said organo-silicon compound is a reaction product of a compound containing acrylyl or substituted acrylyl groups and a silane having a non-hydrolyzable moiety comprising an amino group containing at least one active hydrogen.

44. The two-package system of claim 42, wherein said organo-silicon compound is a reaction product of an amino-compound having at least one active hydrogen and a silane having a non-hydrolyzable moiety comprising acrylyl or substituted acrylyl groups.

45. The two-package system of claim 42, wherein said organo-silicon compound is a reaction product of a silane having a non-hydrolyzable moiety containing an epoxy group and a compound containing a chemical group selected from the group consisting of amino, amide, ureido, urea, urethane, thiol, and hydroxyl, each having at least one active hydrogen atom.

46. The two-package system of claim 42, wherein said organo-silicon compound is a reaction product of an epoxy-containing compound and a silane having a non-hydrolyzable moiety comprising one or more chemical groups selected from the group consisting of primary amino, secondary amino, amide, ureido, urea, urethane and thiol, each having at least one active hydrogen atom.

47. The two-package system of claim 45, wherein said epoxy-containing compound is an aliphatic epoxide and said silane is an aminoalkylsilane.

48. The two-package system of claim 39, wherein said organo-silicon compound is selected from the group consisting of compounds illustrated by the formulae:

49. The two-package system of claim 39, wherein said organo-silicon compound is a reaction product selected from the group consisting of
(a) a reaction product of 1,2-butylene oxide and γ-aminopropyltriethoxysilane;
(b) a reaction product of 1,2-butylene oxide and ureidopropyltriethoxysilne;
(c) a reaction product of 1,2-butylene oxide and mercaptoethyltriethoxysilane; and
(d) a reaction product of 1,4-butanediol diglycidyl ether and γ-aminopropyltriethoxysilane.

50. The two-package system of claim 39, wherein at least one of said compositions further comprises a material selected from the group consisting of fibrous glass, sisal, silica, mica, mineral wool and cotton.

51. The two-package system of claim 39, wherein at least one of said compositions further comprises a thickening agent selected from the group consisting of hydroxyethyl cellulose, hydroxypropyl cellulose, polyethylene oxide and polyvinyl alcohol.

52. The two-package system of claim 39 wherein the level of the organo-silicon compound ranges from about 2 percent to about 5 percent by weight of the magnesium oxide.

* * * * *